(12) United States Patent
Tilstra (10) Patent No.: US 10,702,298 B2
(45) Date of Patent: Jul. 7, 2020

(54) POWERLINE COMMUNICATION SYSTEMS AND METHODS FOR MEDICAL DEVICES

(71) Applicant: Cardiovascular Systems, Inc., St. Paul, MN (US)

(72) Inventor: Matthew W. Tilstra, Rogers, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 582 days.

(21) Appl. No.: 15/440,526

(22) Filed: Feb. 23, 2017

(65) Prior Publication Data

US 2017/0245879 A1     Aug. 31, 2017

Related U.S. Application Data

(60) Provisional application No. 62/300,362, filed on Feb. 26, 2016.

(51) Int. Cl.
*A61B 17/3203* (2006.01)
*A61B 17/3207* (2006.01)
(Continued)

(52) U.S. Cl.
CPC .... *A61B 17/32037* (2013.01); *A61B 17/3207* (2013.01); *A61B 17/320758* (2013.01); *H04B 3/542* (2013.01); *A61B 2017/00017* (2013.01); *A61B 2017/00225* (2013.01); *A61B 2217/007* (2013.01); *A61B 2560/0204* (2013.01); *A61B 2560/0431* (2013.01)

(58) Field of Classification Search
None
See application file for complete search history.

(56) References Cited

U.S. PATENT DOCUMENTS

| | | | |
|---|---|---|---|
| 2004/0243162 A1 | 12/2004 | Wulfman et al. | |
| 2006/0154642 A1* | 7/2006 | Scannell, Jr. | A01G 9/02 455/404.1 |

(Continued)

FOREIGN PATENT DOCUMENTS

| | | |
|---|---|---|
| CN | 203138522 U | 8/2013 |
| WO | 2008/042987 | 4/2008 |

OTHER PUBLICATIONS

International Search Report and Written Opinion of the International Searching Authority dated May 15, 2017 for PCT Application No. PCT/US17/19326, filed Feb. 24, 2017.

(Continued)

*Primary Examiner* — Thienvu V Tran
*Assistant Examiner* — David M Stables
(74) *Attorney, Agent, or Firm* — Barnes & Thornburg LLP; Jeffrey R. Stone (57) ABSTRACT

The Powerline Communication ("PLC") systems and methods described allow for bi-directional communication along an AC or DC conductor between a first device and at least a second device comprising a medical device system. Generally, two devices within a sterile field may communicate with each other by PLC or a first device within a sterile field may communicate with a second device that is outside the sterile field by PLC. More specifically, a controller unit may communicate with a saline, or other fluid, pump to achieve a variety of functional purposes. Similarly, a measurement device may share measured data with another device.

12 Claims, 6 Drawing Sheets

(51) Int. Cl.
*H04B 3/54* (2006.01)
*A61B 17/00* (2006.01)

(56) References Cited

U.S. PATENT DOCUMENTS

| | | |
|---|---|---|
| 2006/0214777 A1 | 9/2006 | Schmitt |
| 2011/0106004 A1 | 5/2011 | Eubanks et al. |
| 2014/0163664 A1* | 6/2014 | Goldsmith ....... A61B 17/00491 623/1.11 |
| 2014/0309658 A1 | 10/2014 | Murphy et al. |
| 2015/0096119 A1* | 4/2015 | Boyle .................. A61G 7/1015 5/87.1 |

OTHER PUBLICATIONS

International Preliminary Report on Patentability issued in related PCT application No. PCT/US2017/019326, dated Sep. 7, 2018.
Extended Search Report issued by European Patent Office dated Sep. 9, 2019.

\* cited by examiner

POWERLINE COMMUNICATION SYSTEMS AND METHODS FOR MEDICAL DEVICES

CROSS-REFERENCE TO RELATED APPLICATIONS

This application claims the benefit of U.S. Provisional Application No. 62/300,362, filed Feb. 26, 2016 and entitled POWER LINE COMMUNICATIONS FOR MEDICAL DEVICES, the entirety of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The disclosure relates generally to systems and methods for implementing communications within a medical device system using powerlines as the communication medium. More specifically, using powerlines as a communication medium within an atherectomy system.

Description of the Related Art

Powerline Communication ("PLC") is a communication technology that uses electricity-providing powerlines as the communication medium, thereby eliminating the need to add additional communication wires. Thus, like other communication technologies, PLC requires a sender/transmitter, a receiver, a communication medium and a signal to be sent by the transmitter over the communication medium to the receiver. The communication medium in PLC is the powerline. The transmitter modulates and then injects the signal into the powerline where it travels to the receiver at the opposing end of the communication link which demodulates the signals and retrieves the data contained therein. The powerline itself may be AC or DC. The communication between a transmitter and a receiver may be bi-directional and may comprise any data that the transmitter and receiver devices may need to exchange. In the bi-directional case, the devices will transmit and receive, thus they may be characterized as transceivers.

PLC systems implement modulation schemes to couple the data to be transmitted onto the AC or DC power conductor or powerline. A variety of modulation schemes exist and are known to the skilled artisan, an exemplary and partial listing follows: OOK (On-Off Keying); ASK (Amplitude Shift Keying); OFDM (Orthogonal Frequency Division Multiplexing); FSK (Frequency Shift Keying); BPSK (Binary Phase Shift Keying); and S-FSK (Spread Frequency Shift Keying).

One focus of the presently described PLC system and method comprises communication between devices that are within one or more medical device systems generally.

More specifically, PLC communications may be implemented within a system for opening occluded blood vessels or biological conduits. Still more specifically, atherectomy procedures are implemented by systems comprising several devices that may require or provide useful information.

For example, rotational atherectomy procedures have become a common technique for removing occlusive or stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. All of the above medical device systems, including but not limited to atherectomy systems and devices, currently comprise either hard-wired or wireless communication solutions between a controller unit or module, for example, and the various elements of the system, some of which may be located a distance away from the controller module. Moreover, the controller module may be located within the sterile field while the device to be communicated with may be outside the sterile field. Wireless communications systems require pairing schemes, they are at risk for cross-talk or binding to another unwanted or unrelated device that may be located in another room and requires certification testing necessary for radio transmitters.

Moreover, we provide disclosure of the following patents and applications, each of which are assigned to Cardiovascular Systems, Inc., and incorporated herein in their entirety, each of which may comprise high-speed rotational atherectomy systems, methods and/or devices that may be used with various embodiments of the presently disclosed subject matter, including but not limited to a handle or controller device in operative communication with a high-speed rotational drive shaft and saline pump:

U.S. Pat. No. 9,468,457, "ATHERECTOMY DEVICE WITH ECCENTRIC CROWN";
U.S. Pat. No. 9,439,674, "ROTATIONAL ATHERECTOMY DEVICE WITH EXCHANGEABLE DRIVE SHAFT AND MESHING GEARS";
U.S. Pat. No. 9,220,529, "ROTATIONAL ATHERECTOMY DEVICE WITH ELECTRIC MOTOR";
U.S. Pat. No. 9,119,661, "ROTATIONAL ATHERECTOMY DEVICE WITH ELECTRIC MOTOR";
U.S. Pat. No. 9,119,660, "ROTATIONAL ATHERECTOMY DEVICE WITH ELECTRIC MOTOR";
U.S. Pat. No. 9,078,692, "ROTATIONAL ATHERECTOMY SYSTEM";
U.S. Pat. No. 6,295,712, "ROTATIONAL ATHERECTOMY DEVICE";
U.S. Pat. No. 6,494,890, "ECCENTRIC ROTATIONAL ATHERECTOMY DEVICE";
U.S. Pat. No. 6,132,444, "ECCENTRIC DRIVE SHAFT FOR ATHERECTOMY DEVICE AND METHOD FOR MANUFACTURE";
U.S. Pat. No. 6,638,288, "ECCENTRIC DRIVE SHAFT FOR ATHERECTOMY DEVICE AND METHOD FOR MANUFACTURE";
U.S. Pat. No. 5,314,438, "ABRASIVE DRIVE SHAFT DEVICE FOR ROTATIONAL ATHERECTOMY";
U.S. Pat. No. 6,217,595, "ROTATIONAL ATHERECTOMY DEVICE";
U.S. Pat. No. 5,554,163, "ATHERECTOMY DEVICE";
U.S. Pat. No. 7,507,245, "ROTATIONAL ANGIOPLASTY DEVICE WITH ABRASIVE CROWN";
U.S. Pat. No. 6,129,734, "ROTATIONAL ATHERECTOMY DEVICE WITH RADIALLY EXPANDABLE PRIME MOVER COUPLING";
U.S. patent application Ser. No. 11/761,128, "ECCENTRIC ABRADING HEAD FOR HIGH-SPEED ROTATIONAL ATHERECTOMY DEVICES";
U.S. patent application Ser. No. 11/767,725, "SYSTEM, APPARATUS AND METHOD FOR OPENING AN OCCLUDED LESION";
U.S. patent application Ser. No. 12/130,083, "ECCENTRIC ABRADING ELEMENT FOR HIGH-SPEED ROTATIONAL ATHERECTOMY DEVICES";

U.S. patent application Ser. No. 12/363,914, "MULTI-MATERIAL ABRADING HEAD FOR ATHERECTOMY DEVICES HAVING LATERALLY DISPLACED CENTER OF MASS";

U.S. patent application Ser. No. 12/578,222, "ROTATIONAL ATHERECTOMY DEVICE WITH PRE-CURVED DRIVE SHAFT";

U.S. patent application Ser. No. 12/130,024, "ECCENTRIC ABRADING AND CUTTING HEAD FOR HIGH-SPEED ROTATIONAL ATHERECTOMY DEVICES";

U.S. patent application Ser. No. 12/580,590, "ECCENTRIC ABRADING AND CUTTING HEAD FOR HIGH-SPEED ROTATIONAL ATHERECTOMY DEVICES";

U.S. patent application Ser. No. 29/298,320, "ROTATIONAL ATHERECTOMY ABRASIVE CROWN";

U.S. patent application Ser. No. 29/297,122, "ROTATIONAL ATHERECTOMY ABRASIVE CROWN";

U.S. patent application Ser. No. 12/466,130, "BIDIRECTIONAL EXPANDABLE HEAD FOR ROTATIONAL ATHERECTOMY DEVICE"; and U.S. patent application Ser. No. 12/388,703, "ROTATIONAL ATHERECTOMY SEGMENTED ABRADING HEAD AND METHOD TO IMPROVE ABRADING EFFICIENCY".

BRIEF SUMMARY OF THE INVENTION

The Powerline Communication ("PLC") systems and methods allow for bi-directional communication along an AC or DC conductor between a first device and at least a second device comprising a medical device system. Generally, two devices within a sterile field may communicate with each other by PLC or a first device within a sterile field may communicate with a second device that is outside the sterile field by PLC. More specifically, a controller unit may communicate with a saline, or other fluid, pump to achieve a variety of functional purposes. Similarly, a measurement device may share measured data with another device.

The figures and the detailed description which follow more particularly exemplify these and other embodiments of the invention.

DETAILED DESCRIPTION OF THE INVENTION

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
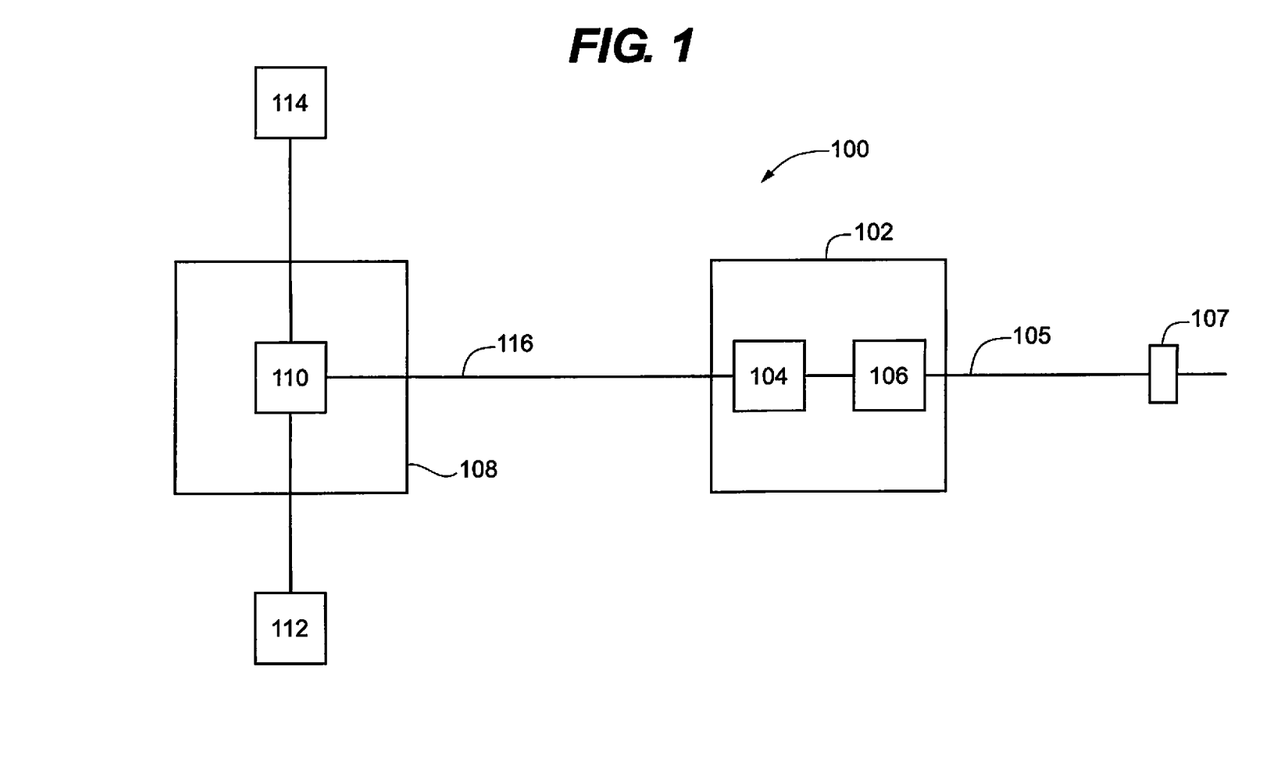
FIG. 1 is a perspective view of one embodiment of a rotational atherectomy device and system of the present invention.

FIG. 1 illustrates an exemplary atherectomy device 100 configured for the present invention. A handle 102 comprises a handle microcontroller 104 in operative communication with a prime mover 106. The prime mover 106 is preferably an electric motor though other solutions are known, e.g., a turbine. Prime mover 106 is in rotatable connection with drive shaft 105 which comprises an abrasive element 107 near a distal end thereof. The device 100 further comprises a fluid pump 108 with a pump microcontroller 110 therein and in operative communication with a fluid reservoir 112.

Power source 114 is in operative communication and connection with the fluid pump 108 and the pump microcontroller 110 via a first power line 115. Fluid pump 108 and pump microcontroller and, in turn, in operative communication and connection with the handle 102 and the handle microcontroller 104, by a second power line 116.

Thus, FIG. 1 illustrates a non-limiting example of implementation of Powerline Communication (PLC) within an atherectomy system and more specifically, between the pump microcontroller 110 and the handle microcontroller 104.

Figure 2:
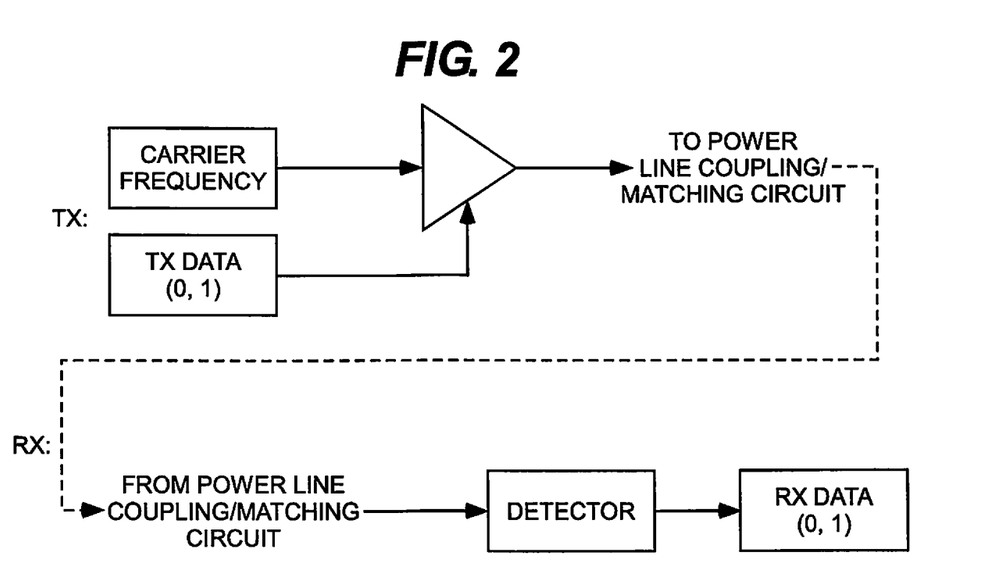
FIG. 2 is a schematic diagram of an exemplary Powerline Communication transmission embodiment.

Turning now to FIG. 2, an exemplary Powerline Communication (PLC") system is provided that may be provided to exchange information between elements or devices within a medical device system such as that of FIG. 1.

FIG. 2 illustrates the transmission portion (TX) and the receiving portion (RX) of the exemplary PLC system. Accordingly, the carrier frequency is provided with the transmitted data stream sent from a transmitter, which may simply be binary data, and that is coupled with the power line via a coupling/matching circuit(s) as is well known to the skilled artisan. Once the transmitted data stream is transmitted from the transmitter and coupled to the power line, the transmitted and coupled data streams along the power line to a detector that may determine if the carrier frequency is present and sets the reception data output accordingly and as is discussed further below.

Figure 3:
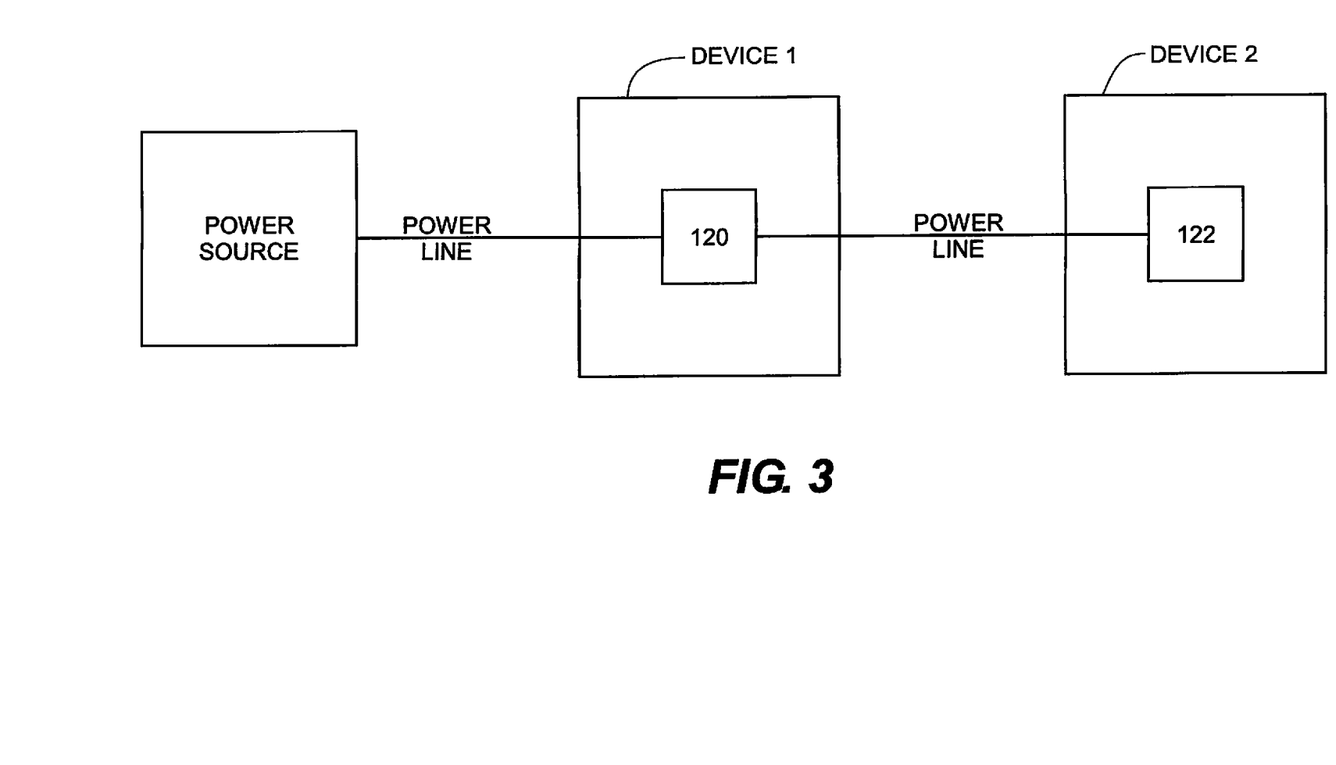
FIG. 3 is a schematic diagram of one embodiment of the present invention.

FIG. 3 illustrates a medical device system comprising at least two devices, device 1 and device 2 as shown. Devices 1 and 2 are coupled operatively with a power line that enables implementation of the PLC system as described herein for bi-directional communication between devices 1 and 2. A first power line is connected with the power source is operatively connected and in operative communication with a first microcontroller 120 located within device 1 which is, in turn, operatively connected and in communication with a second microcontroller 122 within device 2 by a second power line. The microcontrollers 120, 122 are programmed to operate the respective devices and may exchange information/data over the second power line disposed therebetween. One of the devices will preferably be a master to the other device. It will be appreciated that additional devices may be added to the communication system via a power line operative connection to enable further bi-directional communication. Such devices may include separate medical device systems, or components thereof as well as servers or other electrically powered devices capable of communication with the PLC system described herein.

Figure 4:
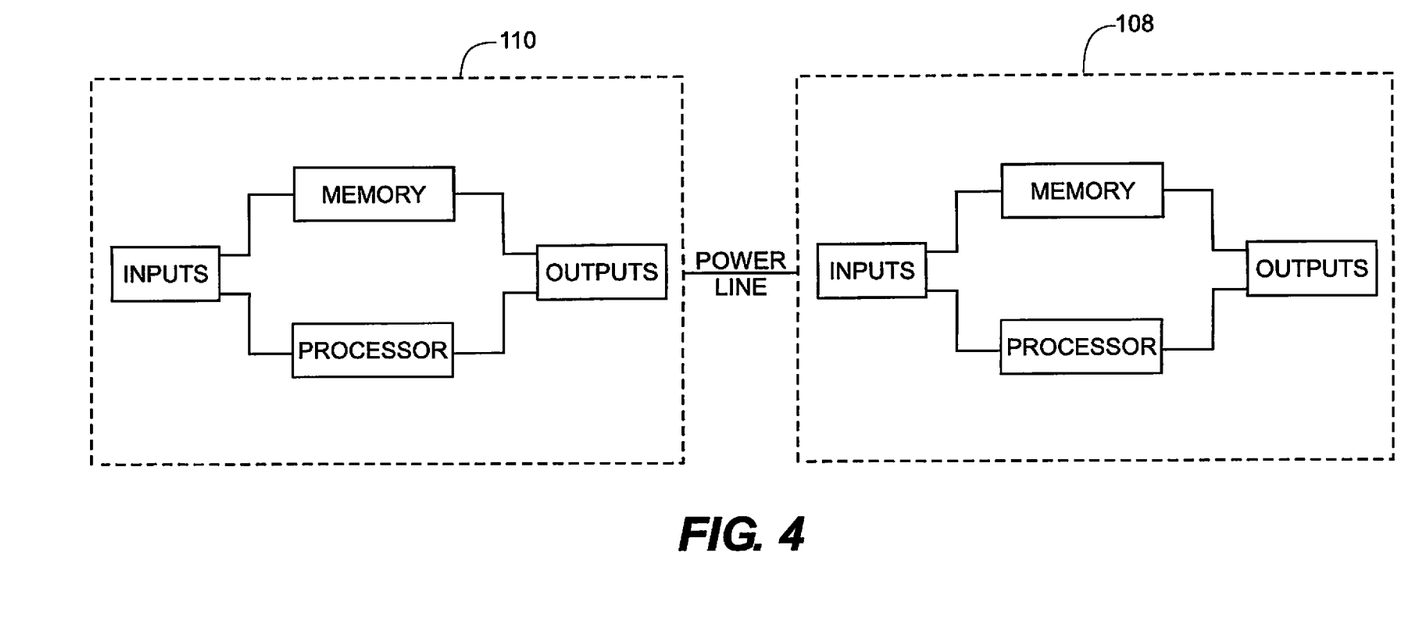
FIG. 4 is a schematic diagram of one embodiment of the present invention.

Turning now to FIG. 4, the microcontroller structure is discussed. We refer back to the microcontrollers 104, 110 of the exemplary atherectomy system in FIG. 1 for simplicity and ease of description. It is understood that the microcontroller structure and function within a PLC system is in no way limited to atherectomy systems and may be applied to medical device communication systems via PLC.

Accordingly, the handle microcontroller 104 and the pump microcontroller each consist of at least the following elements as is well understood by the skilled artisan in operative connection and communication as shown: input ports, output ports, memory and a processor. The memory may comprise pre-populated data and may receive new data written thereto accessible when needed. The processor may comprise programmed instructions or may access programmed instructions stored within the memory and execute the instructions. The data input ports may be used to facilitate the data exchange with the PLC system and/or to allow new information to be loaded by an operator. As shown, the microcontrollers 104, 110 are operatively connected with a power line and enabled to exchange data on the power line via PLC system communication.

We now discuss in detail the PLC communication system and method for the exemplary embodiment of FIG. 1, and with continued reference to FIGS. 2 and 4, illustrating the atherectomy device handle, and controller unit located externally, or alternatively therein, and comprising a power line connection to the pump device(s). Other medical device systems and devices are within the scope of the present invention which is not intended to be limited by the exemplary teaching of the system of FIG. 1.

The PLC interface of FIGS. 1, 2 and 4 within the pump microcontroller 110 employs the power line connection 116 between the pump microcontroller 110 and the handle microcontroller 104 to superimpose a serial data stream on top of the power signal present when power is applied to the power line 116. An exemplary data stream may comprise a 9600 baud 8N1 serial data stream, though other data streams may be used as will be readily recognized by the skilled artisan. The serial stream comprises asserted bits and idle bits of data. The asserted bits and idle bits may be identified or designated in a variety of ways, one exemplary identification method is to designate, represent or identify the asserted bit by the presence of a 2 MHz signal while the idle bit is designated, represented or identified by the absence of a 2 MHz signal. Because the data stream channel is shared for transmission and reception, transmitters may "hear" themselves transmit.

The receiver or reception circuit implements filters and/or detectors to determine if the carrier frequency is present and sets the reception data output accordingly. One such detector in use in the receive circuit may perform an automatic threshold operation that requires training at the beginning of a transmission for a pre-determined period of time. For the exemplary data stream described above, the training period duration comprises approximately one symbol length, or approximately 100 us at 9600 baud. This training period maximizes reception sensitivity by preventing the receiving circuit missing the first bit as it trains and requires a receiver circuit that is tolerant of this type of error.

Correct, error-free, transmissions may be ensured by a retry mechanism describe further below.

Figure 5A:
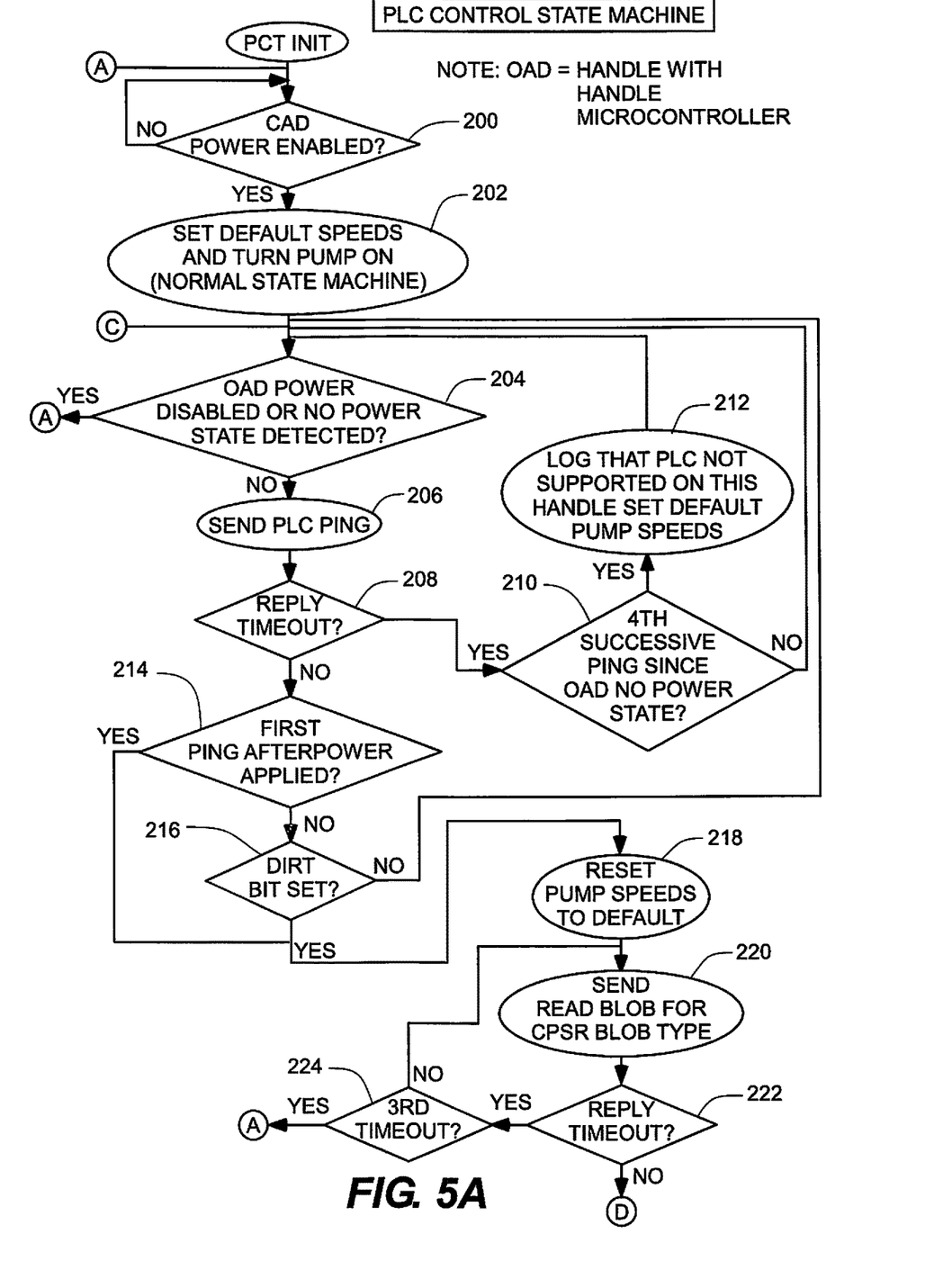
FIG. 5A is part one of a flow diagram of one embodiment of the present invention comprising communication by a pump with a handle/controller device with a Powerline Communication interface.
Figure 5B:
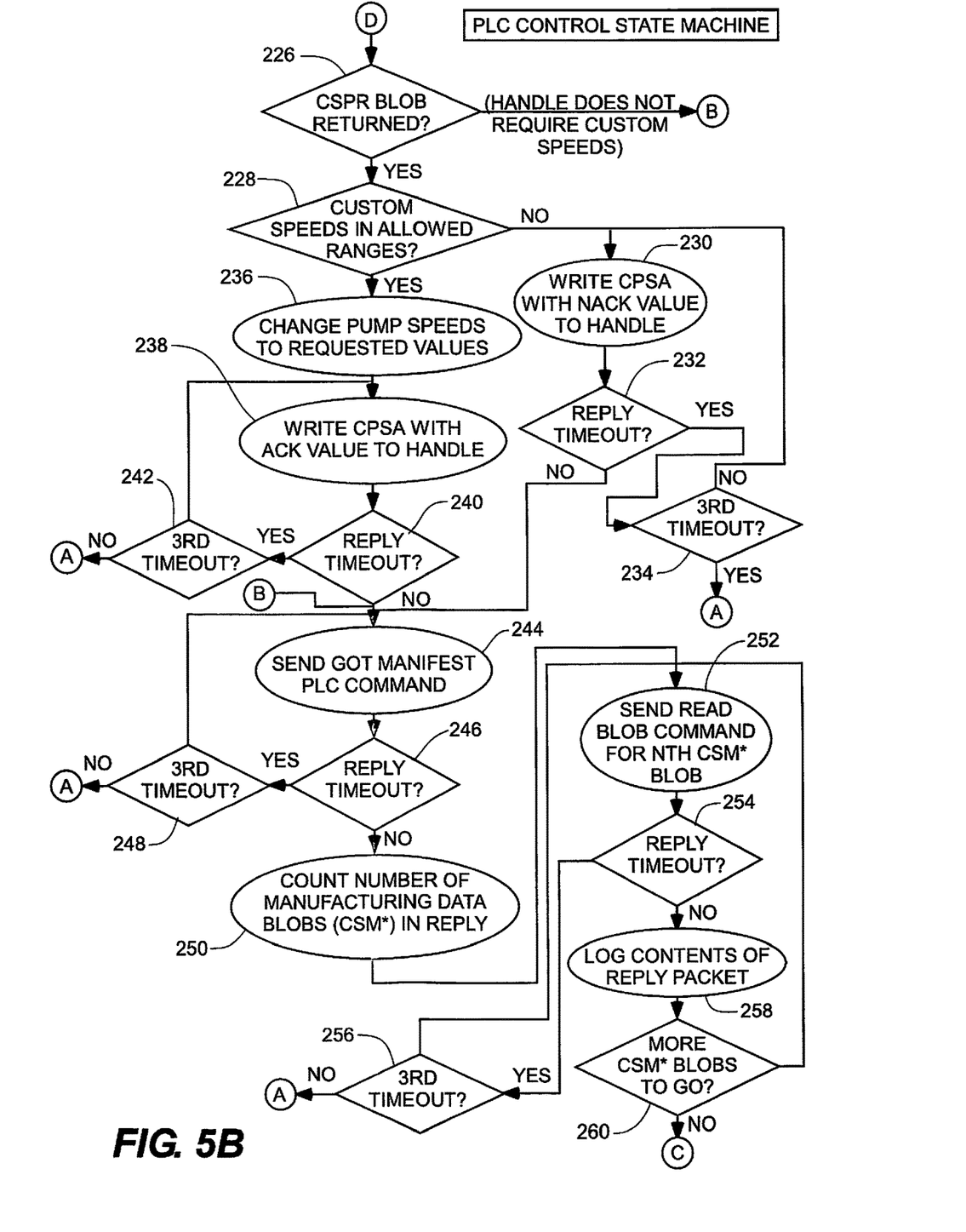
FIG. 5B is part two of the flow diagram of FIG. 5A.

Generally, the data/message flow on the PLC system between the exemplary handle microcontroller 104 and fluid pump microcontroller 110 will now be described with reference to the flow charts 5A and 5B. Note that the nomenclature "OAD" refers to Orbital Atherectomy Device, and is intended to refer to the handle 102, including but not limited to the handle microcontroller 104.

System Initialization

When the pump microcontroller 110 first enables power to the handle 102, the pump microcontroller 110 needs to determine if that handle 102 supports PLC or not. FIGS. 5A and 5B outline the steps necessary for making this determination and will be discussed further below.

The pump microcontroller 110 must go through this determination process each time power is applied to the handle 102 as the handle 102 may have been changed, in whole or in part, while the power was turned off.

If the pump microcontroller 110 determines that the handle 102 does support PLC, the pump microcontroller 110 will go through a series of steps, detailed in FIGS. 5A and 5B, to see if the handle 102 requires custom pump speeds, and then get a list of all of the blob types that are currently stored within the memory of the handle microcontroller 104.

Note that the term "blob" is defined and used herein as a term to describe a generic data container.

The pump microcontroller 110 then may read out all manufacturing data blobs, or generic data containers, and store their contents in a log file on an SD card or the equivalent.

Custom Pump Speeds

The handle microcontroller 104 may request that a pump microcontroller 110 use non-default high and low pump speeds. Because the handle microcontroller 104 never volunteers data via PLC (because the pump microcontroller 110 is always the master and therefore the handle microcontroller 104 only responds to commands sent from the pump microcontroller 110) the pump microcontroller 110 must check to see if the handle microcontroller 104 includes a request for custom speeds by looking for a custom speed blob stored in the memory section of the handle microcontroller 104.

If the pump microcontroller 110 determines that the handle microcontroller 104, and the handle 102, does support PLC, or the pump microcontroller 110 determines that the blob data in memory section of the handle microcontroller 104 may have changed, the pump microcontroller 110 must ask to read the contents of the custom speed blob from the memory section of the handle microcontroller 104.

The pump microcontroller 110 may determine that the handle microcontroller 104, and handle 102, does not/do not require custom pump speeds as follows: there will be no custom speed blob stored in the handle microcontroller 104 and the pump microcontroller 110 will get no response. Alternatively, a custom speed blob response to the pump microcontroller 110 inquiry indicates that the handle microcontroller 104 does require custom speeds. If this custom speed blob type is present the handle microcontroller 104 will reply to a Get Blob Contents request, and the pump microcontroller 110 can then attempt to update the high and low pump head RPM values within its memory section and/or programmed instructions based on the values in the returned blob.

After reading in a custom speed request blob, the pump microcontroller 110 may then write a Custom Pump Speed Acknowledge ("CPSA") blob to the handle microcontroller 104. The pump microcontroller 110 may set the Status field in the CPSA blob to either the Pump Accepted Speeds value or the Pump Rejected Speeds value. This informs the handle microcontroller 104 if (1) the pump microcontroller 110 was able to support its new high and low speed request; or (2) if the pump microcontroller 110 will continue to use default speeds. At that point the handle microcontroller 104 can decide if it should allow spinning of the prime mover 106 and drive shaft 105. In different circumstances the handle microcontroller 104 may decide that the pump microcontroller 110 rejecting its speed request is OK or not OK, depending on the specific logic stored within the memory of that particular handle microcontroller 104.

The acknowledge blob (ACK) will be deleted in the handle microcontroller 104 each time power is lost or the user changes the handle 102 configuration, e.g., a new exchangeable cartridge is inserted into the handle 102, so that each time the handle 102 is powered on or the user modifies the handle 102 configuration, it will go through the evaluation process of determining whether the pump microcontroller 110 supports its custom speed request or not.

After the pump microcontroller 110 has checked for a custom speed blob on the handle microcontroller 104, the pump microcontroller 110 may then proceed to request a blob manifest from the memory in the handle microcontroller 104 which the pump microcontroller 110 may then use to look for other blob types of interest, e.g., the manufacturing data blobs. The reason that pump microcontroller 110 may ask for the custom speed blob before requesting the blob manifest is to learn the new speeds that the handle microcontroller 104 is asking for as quickly as possible. That way, if the user turns the handle microcontroller 104, the pump microcontroller 110 can provide the custom speeds right away.

Reading Back Sent Data

For any blob type that actually stores data on the OAD, the pump microcontroller 110 should always read back the blob that just got written to confirm that the write was successful with the desired values. This is not necessary for blobs like the OAD Custom Pump Speed Acknowledge Blob ("CPSA") that are only used to deliver an informational message to the OAD. The receiver can be updating blob data in between PLC packets, and a write operation over PLC is not disruptive of the receiver's blob integrity.

PLC Ping

Because the handle microcontroller 104 can create, destroy, and modify its blobs during normal operation the pump microcontroller 110 must have a mechanism for detecting changes in the handle microcontroller 104. It does this by periodically sending PLC ping commands to the handle microcontroller 104. The ping response packet from the handle microcontroller 104 includes a Blob Manifest Dirty Bit, which if set, indicates to the pump microcontroller 110 that some blob contents or existence has changed. When the pump microcontroller 110 sees this bit set it needs to restart the blob manifest process as detailed in FIGS. 5A and 5B and discussed below. A handle microcontroller 104 may choose to not set the dirty bit on every blob change, but only on changes that it knows are important to its interaction with the pump microcontroller 110.

Because PLC can be unreliable while the handle 102 and handle microcontroller 104 is performing certain operations (like spinning), the ping command will sometimes fail to be heard by the handle microcontroller 104 and the handle microcontroller 104 will sometimes fail to send successful packets back up to the pump microcontroller 110 in response. This is expected and handled by the ping retry mechanism detailed in FIGS. 5A and 5B and discussed further below.

When the pump microcontroller 110 powers up the handle microcontroller 104, it will send a ping to see if the handle microcontroller 104 replies (and thus supports PLC as discussed above) but it will not care if the dirty bit in that first response is set or not. It will always ask for a custom speed blob, and after that a blob manifest, to retrieve the initial version of the blob data from the handle microcontroller 104.

Exemplary PLC Flowchart for Atherectomy Devices

FIGS. 5A and 5B therefore detail how the pump microcontroller 110 may exchange information with the handle microcontroller 104 over the PLC interface in accordance with the discussion above regarding System Initialization, Custom Pump Speeds, Reading Back Sent Data, and PLC Ping.

Thus, the process flow begins at A with a determination if the handle and microcontroller therein is powered up (200). If the answer is No, the query is reinitiated until a response is received (Yes). Next, at 202 default speeds are set and the pump, and microcontroller therein, is powered up.

Next, the pump microcontroller 110 determines whether the handle 102 power is disabled or if the handle 102 power is not detected (204). If (Yes=no handle or handle power detected), the process reinitiates at A. If (No=handle power present and detected), the pump microcontroller 110 sends a PLC Ping to the handle microcontroller 104 (206) and determines whether a reply from the handle is received within a predetermined reply time (208). If no reply is received (Yes to reply timeout), the pump microcontroller 110 queries whether the current reply timeout is the $4^{th}$ successive no reply timeout to the PLC Ping (210).

If (Yes), the pump microcontroller 110 determines that the handle 102 does not support PLC, that determination is logged within the pump microcontroller 110 and the pump microcontroller 110 sets the pump to default speeds in order to accommodate the non-PLC enabled handle (212). If (No), the process flow moves back to C and reenters step 204 discussed above.

Flowing from step 208 (No) response to the reply timeout, the pump microcontroller 110 determines whether this is the first ping after power is applied (214) to the handle. If the response is (No), the pump microcontroller 110 determines whether a Dirty Bit Set is present (216). If (No), then the process reverts to C and reengages with step 204. If (Yes) to either the query regarding whether this is the first ping after application of power (214) or to the presence of a Dirty Bit Set (216), the pump microcontroller 110 resets the pump speeds to default (218).

At this point, the pump microcontroller 110 sends a Read Blob for CPSR blob type (220) and monitors for a timeout in the handle controller 104 replying (222). If (Yes), the pump microcontroller 110 determines whether the timeout is the third such timeout. If (Yes), the process reverts to A, reengaging at step 200. If (No), steps 220, 222 and 224 are repeated until the third timeout is reached.

If there is no reply timeout detected in step 222, i.e., if a reply is received, the process moves to D (See FIG. 5B). There, the pump microcontroller 110 determines if the CPSR blob is returned by the handle microcontroller 104 (226). If (No), the handle does not require custom speeds and the process moves to B and engaging step 244 discussed further below. If (Yes), the pump microcontroller determines whether the custom speeds are within range (step 228). If (No), the pump microcontroller 110 write CPSA with NACK value to handle microcontroller 104 (230) and monitors for a reply timeout at (232). If (Yes) a reply timeout is received, the pump microcontroller 110 determines if the timeout is the $3^{rd}$ such timeout (234). If (Yes), the process reengages at A, step 200. If (No), the process moves to B and step 244, to be discussed below.

If the answer to step 228 is (Yes), the custom speeds are in the allowed range and the pump controller 110 changes the pump speeds to requested values (236). The pump controller 110 then writes CPSA with ACK value to the handle controller 104 (238) and monitors for a reply timeout (240). If a timeout is received, the pump microcontroller 110 determines if it is the 3$^{rd}$ such timeout (242). If (Yes), the process reverts to A and step 200. If (No), the process reengages and repeats steps 238, 240, 242.

If no reply timeout is received, the pump microcontroller 110, the Get Manifest PLC command is sent (244) and the pump microcontroller 110 monitors for a reply timeout (246). If a timeout is received, the pump microcontroller 110 determines if the timeout is the 3$^{rd}$ such timeout (248). If (Yes), the process reengages at A, step 200. If (No), the process moves to step B and repeats steps 244, 246 and 248.

If no reply timeout is received at (246) the pump microcontroller 110 counts the number of Manufacturing Data blobs sent in reply by the handle microcontroller 104 (250). The pump controller 110 then sends Read Blob commands for each Manufacturing Data blob (CSM) (252) and monitors for a reply timeout (254). If a timeout is received, the pump microcontroller 110 determines if it is the 3$^{rd}$ such timeout (256). If (Yes), the process reverts to A and step 200. If (No), the pump microcontroller 110 determines if any further CSM blobs are to be read (260). If (No), the process reverts to C and step 204. If (Yes), the reverts to step (252).

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A medical device system comprising:
   a first device comprising a microcontroller comprising a memory, processor, input ports and output ports in operative communication;
   a second device comprising a microcontroller comprising a memory, processor, input ports and output ports in operative communication; and
   a power line in operative communication with a power source and further disposed between the microcontroller of the first device and the microcontroller of the second device, the power line in operative connection with a power source and placing the first and second devices in operative connection and communication with each other using the power line as the communication line,
   wherein the first device microcontroller is configured as a master to the second device microcontroller, and
   wherein the first device microcontroller and second device microcontroller are adapted to enable transmission of data to the second device microcontroller and receiving of data from the second device microcontroller over the power line disposed therebetween to determine if the second device is compatible with the first device, and
   wherein the second device microcontroller is adapted to power up with an operative connection to the power source and wherein the first device microcontroller transmits data to the second device microcontroller, receives responsive data from the second device microcontroller, and determines if the second device is compatible with the first device each time the second device is powered up.

2. The medical device system of claim 1, further comprising the second device microcontroller adapted to power up with an operative connection to the power source and wherein the first device microcontroller transmits data to the second device microcontroller, receives responsive data from the second device microcontroller, and determines if the second device is compatible with the first device each time the second device's configuration is changed.

3. The medical device of claim 1, further comprising the first device microcontroller adapted to send data to the second device microcontroller to determine if the second device is capable of communicating over the power line disposed therebetween.

4. The medical device of claim 1, further comprising exchanging data between the first device microcontroller and the second device microcontroller.

5. The medical device system of claim 1, wherein the power line is adapted for DC power transmission.

6. The medical device system of claim 1, wherein the power line is adapted for AC power transmission.

7. An atherectomy system in operative connection with a power source and comprising:
   a fluid pump with a pump microcontroller comprising a memory, processor, input ports and output ports in operative communication with each other;
   a handle comprising a configuration and a handle microcontroller comprising a memory, processor, input ports and output ports in operative communication with each other;
   a power line in operative communication with a power source and disposed between the fluid pump microcontroller and the handle microcontroller, the fluid pump microcontroller adapted and configured as a master to the handle microcontroller and the fluid pump microcontroller and handle microcontroller adapted to communicate with each other over the power line disposed therebetween,
   wherein the fluid pump microcontroller adapted to send data to the handle microcontroller to determine if the handle microcontroller is capable of communicating with the fluid pump microcontroller over the power line disposed therebetween,
   wherein the fluid pump microcontroller and the handle microcontroller adapted to enable transmitting of data to the handle microcontroller from the fluid pump microcontroller and receiving of data from the handle microcontroller transmitted by the fluid pump microcontroller over the power line disposed therebetween to determine if the handle microcontroller is compatible with the fluid pump microcontroller, and
   wherein the fluid pump microcontroller and the handle microcontroller adapted to enable transmitting of data to the handle microcontroller from the fluid pump microcontroller and receiving of data from the handle microcontroller transmitted by the fluid pump microcontroller over the power line disposed therebetween to determine if the handle microcontroller is compatible with the fluid pump microcontroller, and wherein the handle microcontroller is adapted to power up and wherein the fluid pump microcontroller is adapted to transmit data to the handle microcontroller, receive responsive data from the handle microcontroller and determine that the handle microcontroller is compatible with the fluid pump microcontroller each time power is applied to the handle microcontroller to power it up.

8. The atherectomy system of claim 7, further comprising exchanging data between the first device microcontroller and the second device microcontroller.

9. The atherectomy system of claim 8, further comprising the fluid pump microcontroller adapted to determine that the handle microcontroller is not compatible with the fluid pump microcontroller if responsive data is not received from the handle microcontroller when the fluid pump microcontroller transmits data to the handle microcontroller each time power is applied to the handle microcontroller to power it up.

10. The atherectomy system of claim 9, further comprising the fluid pump microcontroller adapted to determine that the handle microcontroller is not compatible with the fluid pump microcontroller if responsive data is not received from the handle microcontroller when the fluid pump microcontroller transmits data to the handle microcontroller each time the handle configuration is changed.

11. The atherectomy system of claim 7, wherein the power line is adapted for DC power transmission.

12. The atherectomy system of claim 7, wherein the power line is adapted for AC power transmission.

* * * * *